US00PP09764P

United States Patent [19]

Utecht

[11] Patent Number: Plant 9,764

[45] Date of Patent: Dec. 24, 1996

[54] GERANIUM PLANT NAMED 'FISBLU'

[75] Inventor: Angelika Utecht, Montabaur, Germany

[73] Assignee: Florfis AG, Binningen, Switzerland

[21] Appl. No.: 518,896

[22] Filed: Aug. 29, 1995

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Foley & Lardner

[57] ABSTRACT

A new and distinct cultivar of geranium named Fisblu, characterized by its hot pink main flower color, with purple and white markings, large single to weakly semi-double flowers, intense green foliage, compact to medium plant habit with umbels well above the foliage, early flower response and rich flowering through the summer.

1 Drawing Sheet

The present invention comprises a new and distinct cultivar of geranium, botanically known as *Pelargonium zonale,* and hereinafter referred to by the cultivar name Fisblu.

Fisblu is a product of a planned breeding program which had the objective of creating new geranium cultivars with pink flower color with markings on petals, intense green foliage, and medium plant habit.

Fisblu was originated from a hybridization made by the inventor Angelika Utecht in a controlled breeding program in Hillscheid, Germany, in 1990. The female parent was the cultivar Fisbluri, disclosed in U.S. Plant Pat. No. 8,712, and characterized by purple pink main flower color with purple and white markings on petals, medium to dark green foliage and medium to tall plant habit. The male parent of Fisblu was the cultivar Blues, disclosed in U.S. Plant Pat. No. 5,373, and having pink flowers with purple eyes, medium green foliage and compact plant habit.

Fisblu was discovered and selected as one flowering plant within the progeny of the stated cross by Angelika Utecht in 1991 in a controlled environment in Galdar, Gran Canaria, Spain. The first act of asexual reproduction of Fisblu was accomplished when vegetative cuttings were taken from the initial selection in Jun. 1991 in a controlled environment in Galdar, Gran Canaria, Spain, by, or under the supervision of, the inventor.

Horticultural examination of plants grown from these cuttings initiated in May, 1992 in Hillscheid, Federal Republic of Germany, and continuing thereafter, has demonstrated that the combination of characteristics as herein disclosed for Fisblu are firmly fixed and are retained through successive generations of asexual reproduction.

Fisblu has not been observed under all possible environmental conditions. The phenotype may vary significantly with variations in environment such as temperature, light intensity and daylength without, however, any variation in genotype. The following observations, measurements, and comparisons describe plants grown in Hillscheid, Federal Republic of Germany under greenhouse conditions which approximate those generally used in commercial practice.

The following traits have been repeatedly observed and are determined to be basic characteristics of Fisblu, which in combination distinguish this geranium as a new and distinct cultivar:

1. Intense pink (hot pink) main flower color, with purple and white markings on the petals.
2. Large, weakly semi-double, open flower form.
3. Intense medium green foliage, normally without zonation.
4. Compact to medium plant habit.
5. Early flower response and rich flowering throughout the summer.

Of the many commercial cultivars known to the present inventor, the most similar in comparison to Fisblu are the parent varieties Fisbluri and Blues. Reference is made to attached Chart A which compares certain characteristics of Fisblu to those same characteristics of Fisbluri and Blues. In general comparison to Fisbluri and Blues, Fisblu has intermediate characteristics, that is, the main flower color is more intense than the pink color of Blues, but has a less bluish hue than Fisbluri. The leaf color is a deeper green than that of Blues, but still in the medium green color range, while Fisbluri has dark green foliage. Flower response is earlier than Fisbluri.

The accompanying color photographic drawing shows typical flower and foliage characteristics of Fisblu, with colors being as true as possible with illustrations of this type.

In the following description, color references are made to The Royal Horticultural Society Colour Chart. The color values were determined indoors from flowers taken from plants grown in a greenhouse in May 1994 in Hillscheid, Federal Republic of Germany.

Classification:

*Botanical.*—A hybrid of the species *Pelargonium zonale* l'Hert.

*Commercial.*—Zonal geranium, cv., Fisblu

Inflorescence

Umbel:

*Shape.*—Almost semi-spherical.
*Average diameter.*—115 mm.
*Average depth.*—65 mm.
*Peduncle length.*—170 mm.
*Peduncle color.*—Green, about 141 C.
*Pedicel length.*—30 mm.
*Pedicel color.*—Medium green, upper end red.
*Number of flowers per umbel.*—19.

Corolla:

*Average diameter.*—49 mm.
*Form.*—Semi-double, almost single.
*Number of petals.*—6–7.
*Number of petaloids.*—1–2.
*Color (general tonality from a distance of three meters).*—Bluish pink.
*Color of upper petals.*—66 C.
*Color of lower petals.*—66 C-61 D.
*Markings.*—On upper petals (57 A-B) and lower petals (45 B).
*Color of lower surface of petals.*—68 A-B or lighter; reddish veins.

*Color of sepals.*—Medium green, red at the base.

*Number of sepals.*—5–6.

Bud:

*Shape.*—Elliptic.

*Color (adaxial).*—Medium green.

*Color (abaxial).*—Pink and a little white.

Reproductive organs:

*Androecium.*—7 fertile anthers and filaments; orange pollen.

*Gynoecium.*—5–6 lobed stigma, rose red style and stigma.

*Seed.*—No seed set observed.

Spring flowering response period: In Hillscheid, Federal Republic of Germany, in 1994 plants of Fisblu had on average 0.9 umbels with at least one flower opened 11 weeks after planting of unrooted cuttings.

Outdoor flower production: The flower count in 1994 in Hillscheid, Federal Republic of Germany indicated about 40 umbels per plant for May through August observation period.

Durability: Good shatter resistance; good rain resistance.

Plant

Foliage:

*Form.*—Kidney-shaped.

*Margin.*—Bicrenated.

*Color of upper surface.*—Medium green, approximately 137 B-C.

*Color of zonation.*—Normally no zonation.

*Tolerance of botrytis.*—Average.

General appearance and form:

*Internode length.*—15 mm.

*Branching pattern.*—1.8 branches per week.

*Height of foliage.*—25 cm (in Jun., 16-week old plants).

CHART A

| | FISBLU | BLUES | FISBLURI |
|---|---|---|---|
| Main flower color (RHS) | 66 C-61D | 58 D | 66 C–D |
| (lower petals) | hot pink | pink | bluish pink |
| Color of foliage | medium grren 137 B | medium green 137 B–C | dark green 137 A |
| Plant: height of foliage | 25 cm | 20 cm | 29 cm |

I claim:

1. A new distinct cultivar of geranium plant named Fisblu, as illustrated and described.

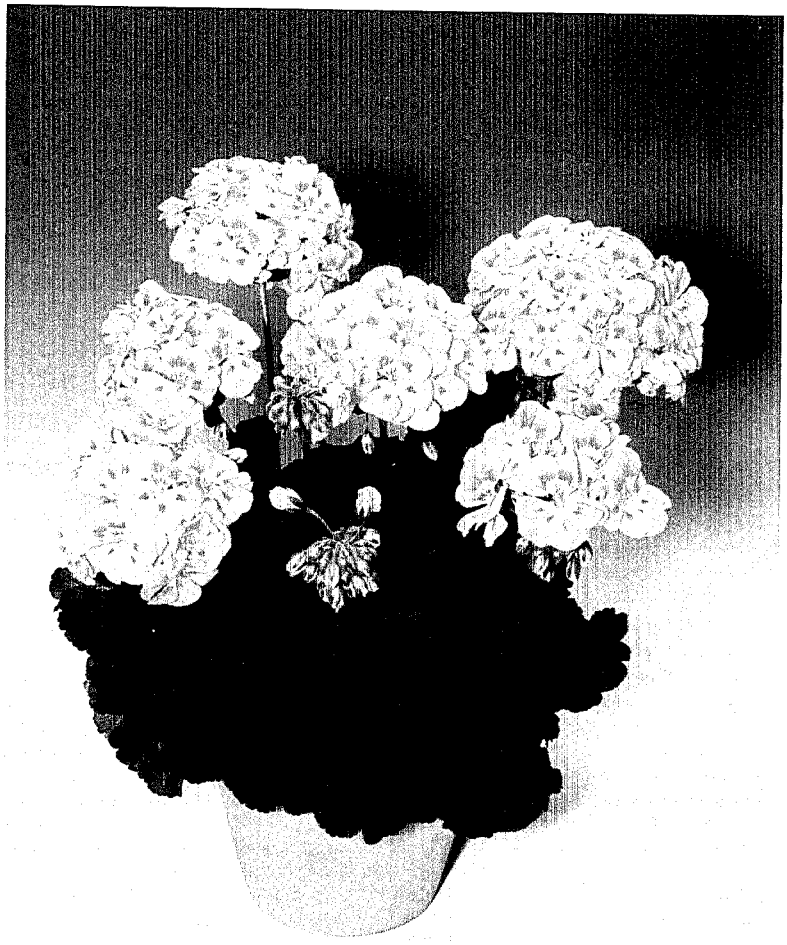

* * * * *